United States Patent
Vora et al.

(10) Patent No.: US 7,919,660 B2
(45) Date of Patent: Apr. 5, 2011

(54) METHODS OF CONVERTING METHANOL FEEDSTOCK TO OLEFINS

(75) Inventors: Bipin V. Vora, Naperville, IL (US); Peter R. Pujado, Kildeer, IL (US)

(73) Assignee: UOP LLC, Des Plaines, IL (US)

( * ) Notice: Subject to any disclaimer, the term of this patent is extended or adjusted under 35 U.S.C. 154(b) by 640 days.

(21) Appl. No.: 12/004,843

(22) Filed: Dec. 21, 2007

(65) Prior Publication Data
US 2009/0163751 A1   Jun. 25, 2009

(51) Int. Cl.
*C07C 1/00* (2006.01)
(52) U.S. Cl. ........ 585/315; 585/330; 585/469; 585/638; 585/639; 585/640; 585/733
(58) Field of Classification Search .................. 585/315, 585/330, 469, 638, 639, 640, 733; 568/671
See application file for complete search history.

(56) References Cited

U.S. PATENT DOCUMENTS

| | | | |
|---|---|---|---|
| 5,191,142 A | 3/1993 | Marshall et al. | |
| 5,573,990 A | 11/1996 | Wang et al. | |
| 7,138,557 B2 | 11/2006 | Senetar | |
| 2004/0215043 A1* | 10/2004 | Senetar | 585/639 |
| 2006/0020155 A1* | 1/2006 | Beech et al. | 585/639 |
| 2006/0135823 A1* | 6/2006 | Jun et al. | 568/671 |

FOREIGN PATENT DOCUMENTS

| | | |
|---|---|---|
| JP | 2007-63270 A | 3/2007 |
| WO | WO 01/21561 A1 | 3/2001 |

* cited by examiner

*Primary Examiner* — Prem C Singh
(74) *Attorney, Agent, or Firm* — Arthur E Gooding

(57) ABSTRACT

A method of converting methanol feedstock to olefins is provided and includes contacting the methanol feedstock in a first conversion zone with a catalyst at reaction conditions effective to produce a first reaction zone effluent comprising DME, unreacted methanol and water, and recycling at least a portion of an overhead vapor product to the first conversion zone and/or to the second conversion zone.

20 Claims, 1 Drawing Sheet

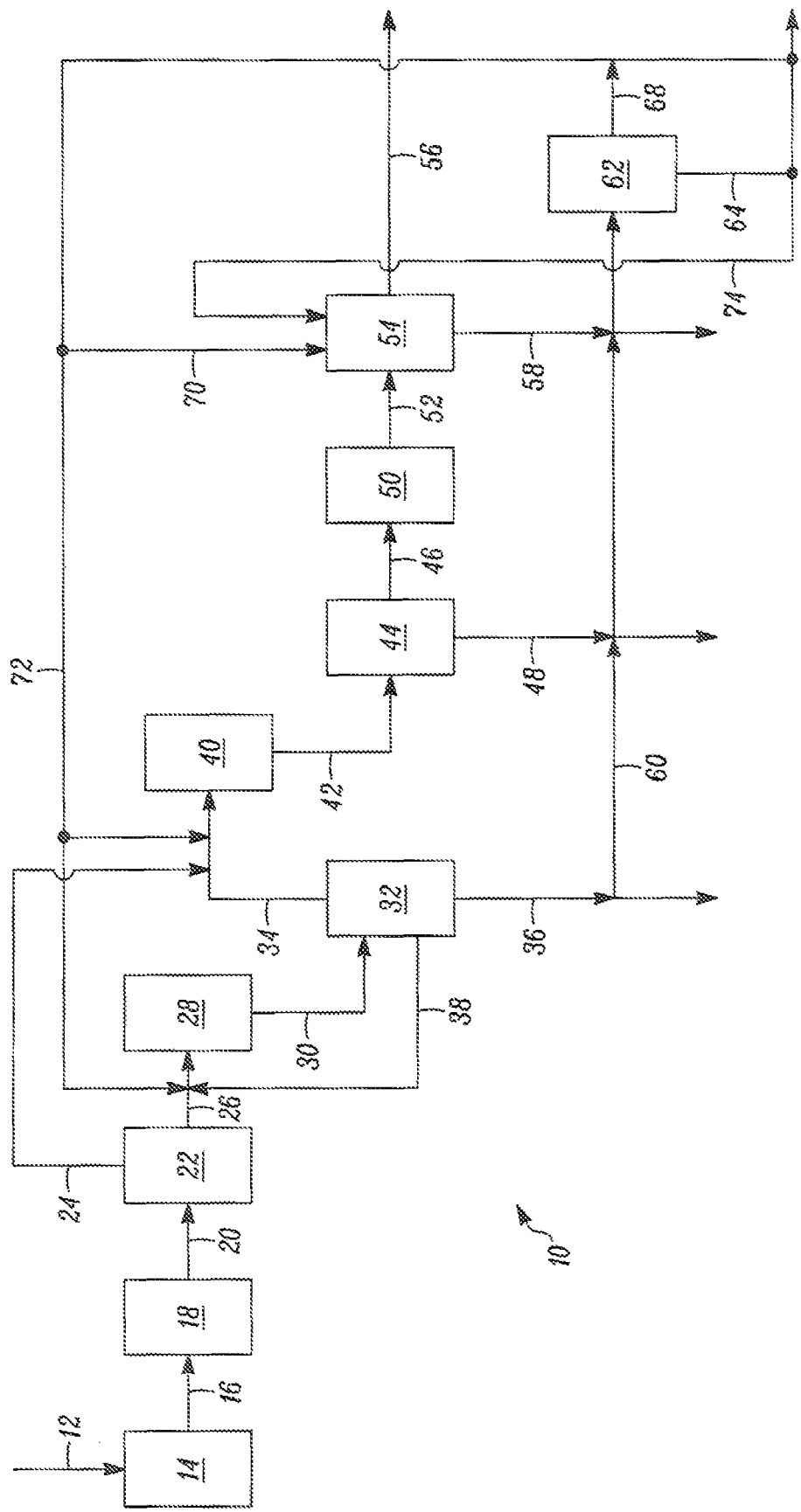

METHODS OF CONVERTING METHANOL FEEDSTOCK TO OLEFINS

TECHNICAL FIELD

This disclosure relates to methods of converting methanol feedstock to olefins.

BACKGROUND

The demand for olefins continues to increase on a worldwide basis. Therefore, more efficient ways of producing such olefins are continuously sought. Methanol, on the other hand, is produced in large quantities throughout the world and is available as a feedstock for olefins. Also, methane and synthesis gas are often times available for use as a feedstock for olefin production. Moreover, there is an increasing demand for environmentally friendly processes which are capable of minimizing reaction by-products that are not capable of being recycled or used in other capacities.

SUMMARY

We provide methods of converting methanol feedstock to olefins comprising: contacting the methanol feedstock in a first conversion zone with a catalyst at reaction conditions effective to produce a first reaction zone effluent comprising DME, unreacted methanol and water; cooling the first reaction zone effluent to separate DME as a first vapor product from the first reaction zone effluent and to form a first aqueous stream comprising water, unreacted methanol, soluble DME and oxygenates; contacting the first vapor product in a second conversion zone with a catalyst at reaction conditions effective to produce a second reaction zone effluent comprising light olefins, unreacted DME, water and oxygenates; cooling the second reaction zone effluent to separate the light olefins and the unreacted DME as a second vapor product from the second reaction zone effluent and to form a second aqueous stream comprising water, soluble DME and oxygenates; compressing the unreacted DME and the light olefins; separating DME from the light olefins with an aqueous absorbing liquid to produce substantially DME free olefins product and a third aqueous stream comprising the absorbing liquid, absorbed DME, soluble oxygenates and hydrocarbons; feeding at least a portion of the first, second and/or third aqueous streams into a stripper and stripping out and recovering the methanol, DME, soluble oxygenates and hydrocarbons as an overhead vapor product and a fourth aqueous stream comprising substantially clean water as a bottoms liquid product; and recycling at least a portion of the overhead vapor product to the first conversion zone and/or to the second conversion zone.

We also provide methods for converting methane to olefins comprising: producing synthesis gas by catalytically reforming methane; producing DME vapor and methanol liquid from the synthesis gas; separating the methanol liquid from the DME vapor; vaporizing the methanol liquid into methanol vapor; contacting the methanol vapor in a first conversion zone with a catalyst at reaction conditions effective to produce a first reaction zone effluent comprising DME, unreacted methanol and water; cooling the first reaction zone effluent to separate the DME as a DME vapor product and produce a first aqueous stream comprising water, unreacted methanol, soluble DME and oxygenates; combining the DME vapor and the DME vapor product into a DME vapor stream product; contacting the DME vapor stream in a second conversion zone with a catalyst at reaction conditions effective to produce a second reaction zone effluent comprising light olefins, unreacted DME, water and oxygenates; cooling the second reaction zone effluent to separate the light olefins and unreacted DME in vapor form and to form a second aqueous stream containing water, soluble DME and oxygenates; compressing the light olefins and the unreacted DME in vapor form; separating compressed DME from compressed light olefins with an absorbing liquid to produce substantially DME free olefins product and a third aqueous stream comprising water, methanol, soluble DME and oxygenates; feeding at least a portion of the first, second and third aqueous streams into a stripper and stripping out and recovering the methanol, the soluble DME and the oxygenates as overhead vapor product and substantially clean water as a bottoms liquid product stream; recycling at least a portion of the overhead vapor product to the first conversion zone and/or the second conversion zone; and recycling at least a portion of the bottoms liquid product stream to convert methane to synthesis gas.

BRIEF DESCRIPTION OF THE DRAWING

The drawing is a schematic representation of one representative example of a system that can be employed to produce olefins.

DETAILED DESCRIPTION

It will be appreciated that the following description is intended to refer to specific examples of a structure selected for illustration in the drawing and is not intended to define or limit the disclosure, other than in the appended claims.

Reference is now made to the FIGURE which is a simplified schematic process flow diagram for a process scheme, generally designated by the reference numeral 10, for the production of olefins from methanol. Those skilled in the art will appreciate that the illustrated process flow diagram has been simplified by eliminating selected typical items of process equipment including but not limited to heat exchangers, process control systems, pumps, valves, controllers, fractionation systems, and the like. It may also be appreciated that the process flow depicted in the FIGURE may be modified in many aspects without departing from the basic overall concept of the processes and the apparatus.

Although the process is generally directed to production of olefins from methanol, it is contemplated that various feedstocks such as, for example, methane and/or synthesis gas may be employed to produce methanol feedstock. Thus, a hydrocarbon or carbonaceous feedstream 12 may comprise a variety of materials, including but not limited to natural gas (mostly methane and ethane), refinery residues, coal and the like and can be processed by conventional means in a synthesis gas production zone 14 such as by steam reformation, partial oxidation, auto thermal reformation and the like to provide a synthesis gas stream 16. Such a synthesis gas stream 16 can in turn be introduced into a synthesis gas conversion reactor zone 18 for contact with catalyst material and at reaction conditions effective to produce a synthesis gas conversion reactor zone effluent that includes dimethyl ether, other synthesis gas conversion products, such as methanol and water and unreacted synthesis gas. The synthesis gas conversion reaction zone effluent 20 can be appropriately separated in a separator 22 to form a stream 24 of dimethyl ether and a stream 26 of methanol.

A feed such as generally composed of at least a portion of the separated product methanol can then be contacted in an oxygenate conversion reactor zone with an oxygenate conversion catalyst and at reaction conditions effective to convert the feed to an oxygenate conversion product stream comprising light olefins as discussed below.

If steam reforming of methane is practiced, the synthesis gas production zone 14 can operate at conventional operating conditions such as at a reaction temperature ranging from about 800° C. to 950° C., a pressure ranging from about 140 psig to about 420 psig, and a water to carbon molar ratio ranging from about 2.0 to about 3.5. In the synthesis gas production zone 14, impurities such as sulfur compounds, nitrogen compounds, particulate matter, and condensibles may be removed in a conventional manner (not shown) to provide the synthesis gas stream 16.

The synthesis gas stream 16 is passed to the synthesis gas conversion reactor zone 18. In the synthesis gas conversion reactor zone 18, at least a portion of the synthesis gas undergoes conversion to form oxygenates such as dimethyl ether (exiting as stream 24) and alcohols (exiting as stream 26) at conditions including a reactor temperature in the range of about 150° C. to about 450° C. at a pressure typically in the range of about 10 psig to about 15,000 psig over a variety of known catalysts such as a mixed metal oxide catalyst of CuO and ZnO, as one example. Of the alcohols, methanol is preferred.

The methanol stream 26 is then fed to a first conversion reactor zone 28. The methanol fed into the first conversion reactor zone produces a conversion reactor zone effluent which comprises dimethyl ether, unreacted methanol and water, for example. The first reactor zone 28 operates under conditions effective to convert methanol to dimethyl ether under conditions including a reactor temperature in the range of about 200° C. to about 300° C. and a pressure of about 50 to about 150 psig. Broader temperature and pressure ranges are possible under selected circumstances. Also, the first conversion reactor zone 28 is preferably a fixed bed reactor containing gamma alumina catalysts with a surface area greater than about 80 m$^2$/gm. Other surface areas may be employed that are less than 80 m$^2$/gm under varying conditions. Also, there are other acidic catalysts, in addition to gamma alumina, that may be employed as desired.

The first conversion reactor zone effluent stream 30 connects to a separation zone 32. The first conversion reactor zone effluent stream 30 entering the separation zone 32 is separated, typically by cooling, at a temperature from about 300° C. to about 40° C. into a dimethyl ether vapor stream 34 and a separator effluent stream 36 which may contain water, methanol, liquid dimethyl ether and miscellaneous oxygenates. Such cooling may be accomplished through one or more heat exchangers in series to maximize heat recovery from the effluent stream 30. Heat energy recovered may be used to preheat the feed stream 26 to the conversion zone 28, or for any other streams as appropriate.

It is, however, possible to separate at least a portion of the methanol portion of the effluent stream 36 with a separator (not shown) and recycle that methanol portion to the first conversion reactor zone 28 via line 38 and a portion of line 26.

Dimethyl ether vapor exiting separator 32 via line 34 enters a second conversion reactor zone 40. It is also possible that at least a portion of the dimethyl ether vapor stream 24 from separator 22 can be introduced into stream 34 so that it can also be at least a portion of feedstock for second conversion reactor zone 40.

Second conversion zone 40 can be any conversion type reactor known in the art that is capable of converting dimethyl ether to light olefins. For example, the temperature in the second conversion zone 40 can be about 300° C. to about 600° C., although temperatures lower and higher may be employed as desired. Similarly, pressures of about 10 to about 100 psig may be employed, although other pressures may also be used. Any number of catalysts may be employed in the second conversion zone 40. However, a fluidized bed reactor containing a SAPO catalyst is preferred. SAPO-34 is particularly a preferred catalyst.

A second conversion reactor zone effluent stream 42 exits second conversion reactor 40 and is passed through one or more heat exchangers in series to maximize heat recovery from stream 42 by cooling the second conversion zone 40 effluent from about 450° C. to about 150° C. When the fluidized bed reactor system is used for the conversion zone 40, it is essential, because an effluent from any fluidized bed system will contain a minor amount of catalyst dust, which is prone to fouling upon condensation, that the effluent stream is maintained above its dew point in cooling through these one or more heat exchangers in series. In such case, the separator 44 is a combination separation quench cooling tower. In separator 44 light olefins and unreacted dimethyl ether are separated from other components in the second conversion reactor zone effluent stream 42 and exit as an effluent stream 46. The separator 44 also produces an effluent stream 48 that includes water and various oxygenates.

The effluent stream 46 is then passed to a compressor 50 which compresses the effluent stream 46. Compression typically depends on the actual stream composition and on the fractionation scheme. If a demethanizer is required, compression may be up to about 3.2 or 3.5 MPa (around 500 psig). If neither a demethanizer nor an acetylene converter is required, the compressor discharge pressure may be dropped to about 2 MPa (about 300 psig). In some situations, it is possible and may be more economical to first compress to the pressure necessary for the DME absorber and then further compress the gaseous effluent to the pressure required for the olefin separation train.

The compressed stream 52 enters absorber 54 which operates at a temperature of about 30° C. to about 100° C. and at a pressure of about 100 psig to about 400 psig. Although these are preferred temperatures and pressures, other temperatures and pressures may be employed to suit operating conditions. The absorbing liquid may be any number of absorbing liquids known in the art. However, water or a water/methanol mixture passed through a gas liquid absorber in a counter-current flow is particularly preferred. Absorber 54 produces a light olefin effluent stream 56 and a recycle effluent stream 58 including absorber fluid, dimethyl ether, various oxygenates, various hydrocarbons and water.

The olefin effluent stream 56 which typically includes ethylene, propylene and/or butylene may then be sent to a conventional fractionation to recover individual pure component products, such as ethylene and propylene which could be channeled to any other use typically known in the art such as, for example, the production of polyolefins such as polyethylene, polypropylene and the like.

On the other hand, at least portions of the effluent stream 36 from separator 32 which comprises a first aqueous stream, the effluent stream 48 from separator 44 which comprises a second aqueous stream and the effluent stream 58 from absorber 54 which comprises a third aqueous stream may be combined into a recycle effluent stream 60 which is sent to a stripper 62. Stripper 62 produces a purified water effluent stream 64 which comprises a fourth aqueous stream, at least a portion of which may be recycled as an absorber fluid to the absorber 54 or used for completely different uses, including further treatment for use in other processes. Stripper 62 also produces a stream 68 essentially containing methanol DME and possibly other light hydrocarbons. Recycle stream 68 may be recycled to conversion zone 28 and/or the conversion zone 40 to maximize light olefins production. It is preferred to recycle the methanol to conversion zone 28 and to recycle the DME to conversion zone 40.

A portion of water effluent stream 64 may be used as an absorbing fluid in absorber 54 by way of line 74.

Although our methods have been described with reference to the above-discussed reactions and structure, it will be understood that modifications and variations are encompassed within the spirit and scope of the disclosure as defined in the appended claims.

What is claimed is:

1. A method of converting methanol feedstock to olefins comprising:
   contacting the methanol feedstock in a first conversion zone with a catalyst at reaction conditions effective to produce a first reaction zone effluent comprising DME, unreacted methanol and water;
   cooling the first reaction zone effluent to separate DME as a first vapor product from the first reaction zone effluent and to form a first aqueous stream comprising water, unreacted methanol, soluble DME and oxygenates;
   contacting the first vapor product in a second conversion zone with a catalyst at reaction conditions effective to produce a second reaction zone effluent comprising light olefins, unreacted DME, water and oxygenates;
   cooling the second reaction zone effluent to separate the light olefins and the unreacted DME as a second vapor product from the second reaction zone effluent and to form a second aqueous stream comprising water, soluble DME and oxygenates;
   compressing the unreacted DME and the light olefins;
   separating DME from the light olefins with an aqueous absorbing liquid to produce substantially DME free olefins product and a third aqueous stream comprising the absorbing liquid, absorbed DME, soluble oxygenates and hydrocarbons;
   feeding at least a portion of the first, second and/or third aqueous streams into a stripper and stripping out and recovering the methanol, DME, soluble oxygenates and hydrocarbons as an overhead vapor product and a fourth aqueous stream comprising substantially clean water as a bottoms liquid product; and
   recycling at least a portion of the overhead vapor product to the first conversion zone and/or to the second conversion zone.

2. The process of claim 1, wherein at least a portion of the absorbing liquid is obtained from the first aqueous stream, the second aqueous stream, and/or the fourth aqueous stream.

3. The process of claim 2, wherein at least a portion of the fourth aqueous stream is recycled to the absorber with other absorbing liquid.

4. The process of claim 1, wherein the temperature in the first conversion zone is about 200 to about 300° C. and the pressure is about 50 about 150 psig.

5. The process of claim 1, wherein the first conversion zone is a fixed bed reactor containing gamma alumina catalyst with a surface area greater than about 80 $m^2$/gm.

6. The process of claim 1, wherein the second conversion zone is a fluidized bed reactor containing silicoaluminophosphate (SAPO) catalyst.

7. The process of claim 1, wherein the temperature in the second conversion zone is about 300 to about 600° C. and the pressure is about 10 to about 100 psig.

8. The process of claim 1, wherein the absorber is in a separation zone at a pressure of about 100 to about 400 psig., and the temperature is about 30 to about 100° C.

9. The process of claim 1, further comprising separating the light olefins into ethylene and propylene.

10. The process of claim 1, wherein the absorbing liquid is water or a water methanol mixture passed through a gas-liquid absorber in a counter-current flow.

11. A process for converting a hydrocarbon or carbonaceous feedstock to olefins comprising:
    producing synthesis gas from the hydrocarbon or carbonaceous feedstock;
    producing DME vapor and methanol liquid from the synthesis gas;
    separating the methanol liquid from the DME vapor;
    vaporizing the methanol liquid into methanol vapor;
    contacting the methanol vapor in a first conversion zone with a catalyst at reaction conditions effective to produce a first reaction zone effluent comprising DME, unreacted methanol and water;
    cooling the first reaction zone effluent to separate the DME as a DME vapor product and produce a first aqueous stream comprising water, unreacted methanol, soluble DME and oxygenates;
    combining the DME vapor and the DME vapor product into a DME vapor stream product;
    contacting the DME vapor stream in a second conversion zone with a catalyst at reaction conditions effective to produce a second reaction zone effluent comprising light olefins, unreacted DME, water and oxygenates;
    cooling the second reaction zone effluent to separate the light olefins and unreacted DME in vapor form and to form a second aqueous stream containing water, soluble DME and oxygenates;
    compressing the light olefins and the unreacted DME in vapor form;
    separating compressed DME from compressed light olefins with an absorbing liquid to produce substantially DME free olefins product and a third aqueous stream comprising water, methanol, soluble DME and oxygenates;
    feeding at least a portion of the first, second and third aqueous streams into a stripper and stripping out and recovering the methanol, the soluble DME and the oxygenates as overhead vapor product and substantially clean water as a bottoms liquid product stream;
    recycling at least a portion of the overhead vapor product to the first conversion zone and/or the second conversion zone; and
    recycling at least a portion of the bottoms liquid product stream to convert methane to synthesis gas.

12. The process of claim 11, wherein at least a portion of the absorbing liquid is obtained from the first and/or second aqueous streams.

13. The process of claim 11, wherein the temperature of the first conversion zone is about 200 to about 300° C. and the pressure is about 50 about 150 psig.

14. The process of claim 11, wherein the first conversion zone is a fixed bed reactor containing gama alumina catalyst with a surface area greater than about 80 $m^2$/gm.

15. The process of claim 11, wherein the second conversion zone is a fluidized bed reactor containing silicoaluminophosphate (SAPO) catalyst.

16. The process of claim 15, wherein the catalyst is SAPO-34.

17. The process of claim 16, wherein the temperature of the second conversion zone is about 300 to about 600° C. and the pressure is about 10 to about 100 psig.

18. The process of claim 11, wherein the absorber is in a separation zone at a pressure of about 100 to about 400 psig., and the temperature is about 30 to about 100° C.

19. The process of claim 11, further comprising separating the olefins into ethylene and propylene.

20. The process of claim 11, wherein the absorbing liquid is water or a water methanol mixture passed through a gas-liquid absorber in a counter-current flow.

* * * * *